United States Patent [19]

Clark, Jr. et al.

[11] Patent Number: 4,781,807

[45] Date of Patent: Nov. 1, 1988

[54] EFFICIENT CIS-TO-TRANS ISOMERIZATION OF 1,4-DIHALOBUTENE-2

[75] Inventors: Clarence E. Clark, Jr., Cincinnati; Richard G. Fayter, Jr., Fairfield, both of Ohio

[73] Assignee: National Distillers and Chemical Corporation, New York, N.Y.

[21] Appl. No.: 936,002

[22] Filed: Nov. 28, 1986

[51] Int. Cl.$^4$ .................... C07C 21/04; C07C 17/00
[52] U.S. Cl. ....................... 204/157.98; 570/236; 204/900
[58] Field of Search ............... 570/236; 204/157.98, 204/900

[56] References Cited

U.S. PATENT DOCUMENTS 2,979,445  4/1961  Lavigne et al. .................. 204/903
4,338,170  7/1982  Murata et al. .................... 204/900

Primary Examiner—Howard T. Mars
Attorney, Agent, or Firm—Kenneth D. Tremain; Gerald A. Baracka

[57] ABSTRACT

This invention relates to an efficient cis-to-trans isomerization of 1,4-dihalobutene-2 by means of a thiol or hydrogen bromide or hydrogen chloride catalyzed reaction.

3 Claims, No Drawings

4,781,807

EFFICIENT CIS-TO-TRANS ISOMERIZATION OF 1,4-DIHALOBUTENE-2

BACKGROUND OF THE INVENTION

The condensation of 1,4-dihalobutene-2 such as 1,4-dichlorobutene-2, with lower alkyl malonic esters such as dimethyl malonate is widely used in industry to prepare various vinylcyclopropane derivatives such as dimethyl 2-vinylcyclopropane-1,1-dicarboxylate which has utility in a wide variety of industrial applications.

The starting material for this condensation, 1,4-dichlorobutene-2 as a commercial product, is usually composed of three isomeric dichlorobutenes, trans-1,4-dichlorobutene-2, cis-1,4-dichlorobutene-2 and 3,4-dichlorobutene-1. Trans-1,4-dichlorobutene-2 is the preferred starting material as the stereochemistry of the intermediate (I) is such that the desired dimethyl 2-vinylcyclopropane-1,1-dicarboxylate is the exclusive product. This is illustrated in Mechanism I below:

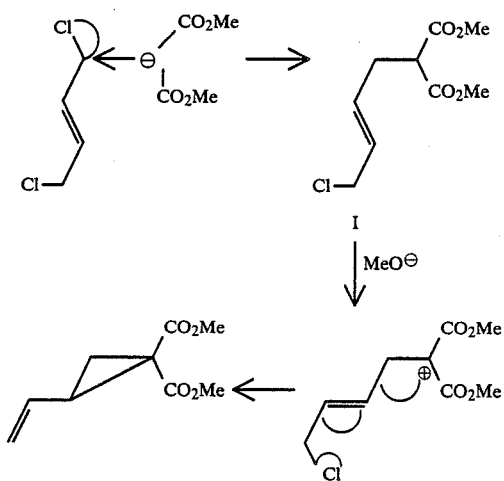

Cis-1,4-dichlorobutene-2 gives two products, dimethyl 2-vinylcyclopropane-1,1-dicarboxylate and dimethyl cyclopent-3-ene-1,1-dicarboxylate in nearly equal amounts as shown in Mechanism II below.

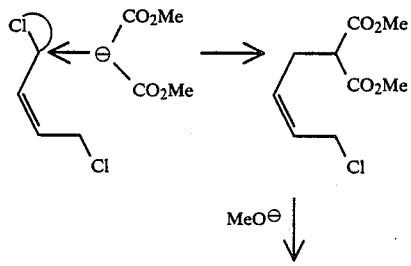

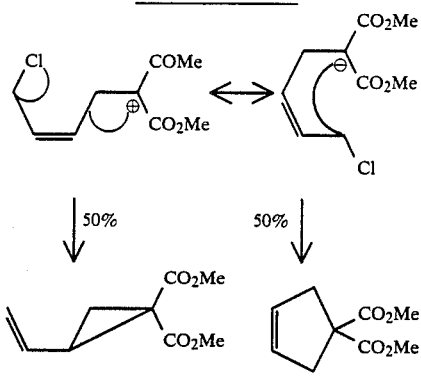

It is nearly impossible to separate dimethyl cyclopent-3-ene-1,1-dicarboxylate from the desired dimethyl 2-vinylcyclopropane-1,1-dicarboxylate by any reasonable means. In the described condensation reaction the third isomer, 3,4-dichlorobutene-1 gives only useless elimination products.

Fractional distillation of the three dichlorobutene isomers can readily be accomplished, but this is an expensive process and leads to the additional difficulty and cost of disposing of 3,4-dichlorobutene-1 and cis-1,4-dichlorobutene-2.

Efforts have been made in terms of isomerizing cis-1,4-dichlorobutene-2 to trans-1,4-dichlorobutene-2, but these methods have met with only moderate success.

Heterogeneous iron, tin and copper compounds as well as onium salts have been reported in the literature as dichlorobutene isomerization catalysts. A typical process employing a copper catalyst is disclosed in U.S. Pat. No. 2,911,450. However, such processes are not completely satisfactory as they either have proven to be ineffective in some instances or have given equilibrium mixtures of all three dichlorobutenes.

The use of thiols as cis-to-trans-olefin isomerization catalysts has also been reported in the literature. See, W. G. Niehaus, Jr., *Bioorg. Chem.*, 3(3), 302–10 (1974) and C. Walling, et al., *J. Amer. Chem. Soc.*, 81, 1144–8(1959) as has hydrogen bromide-catalyzed isomerization. See N. P. Neureiter, et al., *J. Amer. Chem. Soc.*, 82, .5354–8 (1960). However, the thiol-catalyzed and hydrogen bromide-catalyzed isomerization of olefins typically leads to an equilibrium mixture of approximately 80% trans- and 20% cis-olefin. This appears to be true regardless of whether the starting olefin is cis or trans. See C. Walling, et al. Ibid.

It would be highly desirable, therefore, if an improved process could be developed which would permit an efficient cis-to-trans isomerization of 1,4-dichlorobutene-2 so that a high trans (>90%) mixture could be obtained from the usual commercial mixture of 1,4-dichlorobutene-2, which normally has a trans/cis ratio of 77/23, or from other mixtures having even lower trans content without any of the attendant disadvantages of the prior art.

It would also be highly desirable to provide a product with a high content of trans-1,4-dichlorobutene-1 and being substantially free from the other two isomers, cis-1,4-dichlorobutene-2 and 3,4-dichlorobutene-2, which in the described condensation reaction with malonic esters either give approximately equal amounts of the desired dimethyl 2-vinylcyclopropane-1,1-dicarboxylate and the unwanted dimethyl cyclopent-3-ene-1,1-dicarboxylate or in the case of the isomeric 3,4-dichlorobutene-1 only useless elimination products.

BRIEF SUMMARY OF THE INVENTION

We have now discovered that it is possible to produce an efficient cis-to-trans isomerization of 1,4-dichlorobutene-2 so as to provide a high trans content greater than 90% which is eminently suitable for condensation with malonic esters to provide excellent yields of dimethyl 2-vinylcyclopropane-1,1-dicarboxylate with greater than 95% purity and with substantial elimination of 3,4-dichlorobutene-1.

DETAILED DESCRIPTION OF THE INVENTION

The present invention is based upon the discovery that mixtures of cis-and-trans-1,4-dichlorobutene-2 can be rapidly isomerized to mixtures containing very high levels of trans-1,4-dichlorobutene-2 under very mild conditions. The isomerization is accomplished under the catalytic influence of thiols or anhydrous hydrogen bromide or hydrogen chloride with ultraviolet light and/or chemical initiators so that an 80/20 trans/cis mixture is isomerized to a 95/5 trans/cis mixture in as little as ten minutes.

The temperature of the reaction is not critical and may conveniently be from room temperature up to 80° C. or higher depending upon the catalyst employed for the isomerization.

Likewise, the amount of catalyst is not critical and may conveniently be from 0.5 mole % based on the weight of the dichlorobutene to about 20 mole % and preferably from 5 mole % to 10 mole %.

The time of the reaction is likewise not critical and depends to some extent upon the catalyst employed for the isomerization. Thus with the thiol catalyzed isomerization the time may range from 30 minutes to an hour or more at reaction temperatures of from 70° C. to 90° C. whereas with the anhydrous hydrogen bromide or chloride catalyzed isomerization the time is frequently from twenty to thirty minutes or so at temperatures preferably at about room temperature.

With both the thiol catalyzed and hydrogen bromide or chloride catalyzed isomerizations, ratios better than 93/7 trans/cis- dichlorobutene-2 have consistently been obtained with 95-97% recovery of the dichlorobutene-2.

Typical throls useful in the described isomerization reaction are 2-mercaptoethanol, thiophenol, thiolacetic acid, methanethiol, thioglycolic acid, mercaptosuccinic acid, etc.

In the thiol catalyzed isomerization of the dihalobutenes as well as in the anhydrous hydrogen bromide or chloride isomerization reaction it is necessary to employ an initiator for the reaction. Typical chemical initiators may be, for example, 2,2'-azobisisobutyronitrile (AIBN), benzoyl peroxide, t-butyl peroxide, etc.

The amount of chemical initiator employed in the reaction is not critical but must be present in sufficient amount to initiate the reaction. Typically from about 0.1 mole % to about 5 mole % based on the weight of the dichlorobutene has been found to be effective.

As indicated above, 2-mercaptoethanol as the catalyst and 2,2'-azobisisobutyronitrile (AIBN) as the initiator are preferred and have been found to be highly useful in the isomerization of dichlorobutene as they consistently provide ratios greater than 93/7 or higher trans/cis- dichlorobutene with 95-97% recovery of the dichlorobutenes.

Hydrogen bromide with either AIBN or ultraviolet light has also been found to be effective in producing remarkably high trans/cis (95/5) ratios of dichlorobutene at room temperature.

Hydrogen bromide is the preferred catalyst in the described reaction and has been found to be equally effective with either AIBN or ultraviolet light initiation. However, 2-mercaptoethanol with ultraviolet light and hydrogen chloride with ultraviolet light showed marginal activity and hydrogen iodide and $I_2$ showed no catalytic activity with either AIBN or ultraviolet light.

While the present invention has been described hereinabove and in the examples which follow as being particularly applicable to 1,4-dichlorobutene-2 and 1,4-dibromobutene-2, it is to be understood that the isomerization reaction described is applicable to a wide variety of 1,4-dihalobutenes-2 including the following which are exemplary only and it is to be understood that the present invention is not limited thereto:

1,4-dichloro-2-methylbutene-2; 1,4-dibromo-2-methylbutene-2;
1,4-dichloro-2,3-dimethylbutene-2; 1,4-dibromo-2,3-dimethylbutene-2;
1,4-dichloropentene-2; 1,4-dibromopentene-2;
1,4-dichloro-4-methylpentene-2;
1,4-dibromo-4-methylpentene-2;

As indicated above, 1,4-Dichloro- and 1,4-dibromobutene-2 are particularly useful for the present process in view of their commercial availability, reactivity and ability to yield highly useful vinylcyclopropane derivatives.

The invention will be described in greater detail in conjunction with the following specific examples in which the parts are by weight unless otherwise specified.

EXAMPLE 1

Isomerization of Dichlorobutene with 2-Mercaptoethanol and 2,2'-Azobisisobutyronitrile (AIBN)

To 10 mL of 1,4-dichlorobutene-2 was added 0.5 mL of 2-mercaptoethanol (7.5 mole % based on 1,4-dichlorobutene-2) and 0.15 g of AIBN (0.97 mole %). The reaction was then stirred at 80° C. with the following results:

| 0 minutes | 80.5/19.2 trans/cis |
|---|---|
| 15 minutes | 88.9/8.5 trans/cis |
| 30 minutes | 91.0/6.7 trans/cis |

EXAMPLE 2

Isomerization of Dichlorobutene with HBr and UV Light

Approximately 100 mL of 1,4-dichlorobutene-2 was saturated with anhydrous HBr by subsurface introduction through a fritted glass gas dispersion tube. HBr addition was terminated when persistent fumes were visible above the liquid surface. The mixture was then stirred at ambient temperature while being irradiated with a Pen-Ray* lamp with the following results:

78-90% recovery of 1,4-dibromobutene-2 were obtained. The results are shown in Table 2 below.

TABLE 2

Isomerization of Dibromobutenes

| Catal.[1] | Cat. Level[2] | Init.[1] | Init. Level[2] | Rxn. Temp. | Time[3] | Product distribution[4] | | |
|---|---|---|---|---|---|---|---|---|
| | | | | | | t-1,4 | c-1,4 | other[5] |
| 2-ME | 7.5 | AIBN | 0.96 | 80° | 0 | 17.3 | 74.9 | 4.2 |
| | | | | | 30 | 75.1 | 12.7 | 11.3 |
| 2-ME | 7.5 | AIBN | 0.96 | 80° | 0 | 18.2 | 74.6 | 2.8 |
| | | | | | 30 | 77.4 | 12.8 | 9.8 |
| HBr | — | AIBN | 2.0 | 60° | 0 | 13.4 | 83.2 | 3.4 |
| | | | | | 10 | 18.2 | 77.2 | 4.7 |
| HBr | — | AIBN | 2.0 | 60° | 0 | 44.9 | 36.6 | 17.6 |
| | | | | | 20 | 65.3 | 18.6 | 16.1 |
| HBr | — | UV | — | 28° | 0 | 27.0 | 58.3 | 14.7 |
| | | | | | 15 | 65.1 | 13.1 | 21.8 |

[1]2-ME = 2-mercaptoethanol; AIBN = 2,2'-azobisisobutyronitrile; UV = 253.7 nm. ultraviolet light
[2]Mole percent based on dibromobutene
[3]Reaction time in minutes
[4]Area percent by packed column GC analysis; t-1,4 = trans-1,4-dibromobutene-2; c-1,4 = cis-1,4-dibromobutene-2
[5]Unidentified, but probably 3,4-dibromobutene-1

| | |
|---|---|
| 0 minutes | 76.6/22.9 trans/cis |
| 5 minutes | 90.9/5.4 trans/cis |
| 10 minutes | 90.4/5.1 trans/cis |

* 2.5 watts output with 80-90% of radiation at 253.7 nm.

EXAMPLE 3

Following the procedure of Examples 1 and 2, the isomerization of 1,4-dichlorobutene was carried out with the results as shown in Table 1 below.

TABLE 1

Isomerization of Dichlorobutenes

| Catal.[1] | Cat. Level[2] | Init.[1] | Init. Level[2] | Rxn. Temp. | Time[3] | Product distribution[4] | | |
|---|---|---|---|---|---|---|---|---|
| | | | | | | t-1,4 | c-1,4 | other[5] |
| 2-ME | 7.5 | none | — | 80° C. | 0 | 78.8 | 21.2[6] | — |
| | | | | | 180 | 81.8 | 18.2[6] | — |
| 2-ME | 7.5 | AIBN | 0.96 | 80° | 0 | 80.5 | 19.2 | 0.3 |
| | | | | | 30 | 91.0 | 6.7 | 2.3 |
| 2-ME | 0.5 | AIBN | 0.5 | 90° | 0 | 76.7 | 22.4 | 0.9 |
| | | | | | 60 | 80.1 | 19.1 | 0.8 |
| 2-ME | 7.5 | UV | — | 80° | 0 | 78.2 | 21.8[6] | — |
| | | | | | 180 | 86.8 | 13.2[6] | — |
| HBr | — | AIBN | 2.0 | 58° | 0 | 73.6 | 21.3 | 5.1 |
| | | | | | 10 | 90.0 | 7.0 | 3.0 |
| HBr | — | UV | — | 25° | 0 | 76.6 | 22.9 | 0.5 |
| | | | | | 10 | 90.4 | 5.1 | 4.5 |
| HBr | — | UV | — | 40° | 0 | 6.8 | 91.3 | 1.9 |
| | | | | | 5 | 89.7 | 6.0 | 4.2 |
| HCl | — | AIBN | 2.0 | 80° | 0 | 75.0 | 22.1 | 2.9 |
| | | | | | 10 | 75.1 | 21.9 | 3.0 |
| HCl | — | UV | — | 70° | 0 | 79.4 | 19.0 | 1.6 |
| | | | | | 20 | 82.7 | 15.1 | 2.2 |

[1]2-ME = 2-mercaptoethanol; AIBN = 2,2'-azobisisobutyronitrile; UV = 253.7 nm ultraviolet light.
[2]Mole percent based on dichlorobutene.
[3]Reaction time in minutes
[4]Area percent by packed column GC analysis; t-1,4 = trans-1,4-dichlorobutene-2; c-1,4 = cis-1,4-dichlorobutene-2.
[5]Unidentified, but probably 3,4-dichlorobutene-1.
[6]Product distributions for these two reactions are trans/cis ratios.

EXAMPLE 4

Following the procedure of Examples 1 and 2, the isomerization of 1,4-dibromobutene-2 was carried out. Under the influence of the catalyst/initiator combinations of 2-mercaptoethanol/AIBN, 2-ME/UV light, and HBr/UV light, trans/cis-1,4-dibromobutene-2 product ratios ranging from 71/29 to 87/13 with C. and for a sufficient time wherein the final mixture contains at least 90% trans-1,4-dichlorobutene-2.

What is claimed is:

1. A process for isomerizing 1,4-dichlor-butene-2 to provide a high ratio of trans-to-cis-1,4-dichlorobutene-2 which comprises contacting a mixture of trans-1,4-dichlorobutene-2 and cis-1,4-dichlorobutene-2 with anhydrous hydrogen bromide catalyst and an initiator, selected from the group consisting of 2,2'-azobisisobutyronitrile and ultraviolet light, for the reaction at a temperature of from about 25° C. to about 80°

2. The process according to claim 1 in which the initiator is 2,2'-azobisisobutyronitrile.

3. The process according to claim 1 in which the initiator is ultraviolet light.

* * * * *